US00PP35054P2

(12) United States Plant Patent
Hansen

(10) Patent No.: US PP35,054 P2
(45) Date of Patent: Mar. 21, 2023

(54) ***DIANTHUS* PLANT NAMED 'PINKY PROMISE'**

(50) Latin Name: ***Dianthus* hybrid**
Varietal Denomination: Pinky Promise

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 17/803,684

(22) Filed: Oct. 13, 2022

(51) Int. Cl.
*A01H 5/02* (2018.01)
*A01H 6/30* (2018.01)

(52) U.S. Cl.
USPC ..... Plt./277
CPC ..... *A01H 6/305* (2018.05)

(58) Field of Classification Search
USPC ..... Plt./277
CPC ..... A01H 6/305; A01H 5/02
See application file for complete search history.

*Primary Examiner* — Keith O. Robinson

(57) ABSTRACT

A new and unique plant cultivar of perennial carnation or pinks, *Dianthus* plant named 'Pinky Promise' with numerous, single, lightly-sweet fragrant flowers producing a full rounded face. Each flower has five overlapping petals that are fuchsia-pink colored with small darker red bar in the center. Petals have moderate dentate apices. Flowering season is strong for four weeks beginning in late spring nearly completely covering the dome of the plant. The habit is compact, heavily branched, moderately spreading, and dense, with lightly glaucous blue-green foliage.

1 Drawing Sheet

Botanical denomination: *Dianthus* hybrid.
Cultivar designation: 'Pinky Promise'.

STATEMENT REGARDING PRIOR DISCLOSURES UNDER 37 CFR 1.77(b)(6)

The first enabling disclosure as a sale of the new plant was on Oct. 22, 2021, by Green Leaf Plants® (a division of Aris Horticulture, Inc.) which obtained the new plant from Walters Gardens, Inc. Walters Gardens, Inc. also introduced the new plant on Feb. 1, 2022, in the form of photographs and a brief description on a website operated by Walters Gardens, Inc. followed on Jun. 8, 2022, as a photograph and brief description in the "Walters Gardens 2022-2023 Catalog." Walters Gardens, Inc. obtained the plant and all information relating thereto, from the inventor. No plants of *Dianthus* 'Pinky Promise' have been sold, in this country or anywhere in the world, nor has any disclosure of the new plant been made more than one year prior to the filing date of this application, and such sale or disclosure within one year was either derived directly or indirectly from the inventor and would therefore be a 35 U.S.C. § 102b exception.

BACKGROUND OF THE INVENTION

The present invention relates to the new and distinct cultivar of carnation or pinks from the genus *Dianthus* and was given the cultivar name 'Pinky Promise'. The new plant was the result of an intentional cross on Oct. 21, 2014, under the direction of the inventor between the proprietary, unreleased, unnamed hybrid known only by the breeder code 11-265-1 (not patented) as the female or seed parent and the male or pollen parent is the proprietary, unreleased, unnamed hybrid known only by the breeder code 12-60-1 (not patented). The cross was harvested and sown in the early spring of 2015. The new hybrid was first selected from trials at a wholesale perennial nursery in Zeeland, Mich. during the summer of 2017 as a single seedling clone and given the breeder code number 14-44-1 later in the evaluation processes. *Dianthus* 'Pinky Promise' has been asexually propagated at the same nursery in Zeeland, Mich. since 2017 using traditional shoot tip cutting procedures and later sterile shoot-tip tissue culture and found to reproduce plants that are identical and exhibit all the characteristics of the original plant in successive generations.

SUMMARY OF THE INVENTION

*Dianthus* 'Pinky Promise' has not been evaluated under all possible environmental conditions. The phenotype may vary with variations in the environment including: growing temperature, available sunlight, nutrition, water, etc. without a change in the genotype of the plant.

The closest comparison plants to the new plant known to the inventor include: 'Paint the Town Magenta' U.S. Plant Pat. No. 29,222, 'Paint the Town Fuchsia' U.S. Plant Pat. No. 28,636, KAHORI® 'Pink' (not patented), 'Zing Rose' (not patented).

'Paint the Town Magenta' has a similar habit and size, but the foliage is more glaucous, and the flowers are vibrant magenta-pink without the lighter center eye. 'Paint the Town Fuchsia' has a similar habit and size, but the foliage is more glaucous and the flowers are more fuchsia-colored. KAHORI® 'Pink' has smaller size and less dense habit, the flowers are more pinkish near white styles, and the individual petals are narrower with less overlapping. 'Zing Rose' is less compact, has smaller flowers, the flowers are more magenta, the petals have less overlapping, and there is a thin darker red eye.

The female parent, 11-265-1, has a more open habit, smaller flowers and wider leaves that were more green. The male parent, 12-60-1, had larger flowers, longer narrower leaves and more compact habit.

*Dianthus* 'Pinky Promise' is distinct from its parents and all other *Dianthus* known to the applicant in the following combined traits:

1. Single flowers with five overlapping petals forming a full rounded face;
2. Petals have a moderately serrated apex;
3. Petal color is a soft fuchsia-pink with slightly darker veins near the center;
4. Numerous flowers per plant on dense, heavily-branched, upright stems;
5. Flowering period in a strong flush in late spring following vernalization nearly completely covering dome of the plant;
6. Compact, dense and moderately spreading habit with lightly-glaucous, foliage.

BRIEF DESCRIPTION OF THE DRAWINGS

The photographs of 'Pinky Promise' are of a two-year-old plant grown in a full-sun trial garden in Zeeland, Mich. showing the overall appearance of the plant including the unique traits. The colors are as accurate as reasonably possible with color reproductions. Some slight variation of color may occur as a result of lighting quality, intensity, wavelength, direction, or reflection.

DETAILED DESCRIPTION OF THE PLANT

Figure 1:
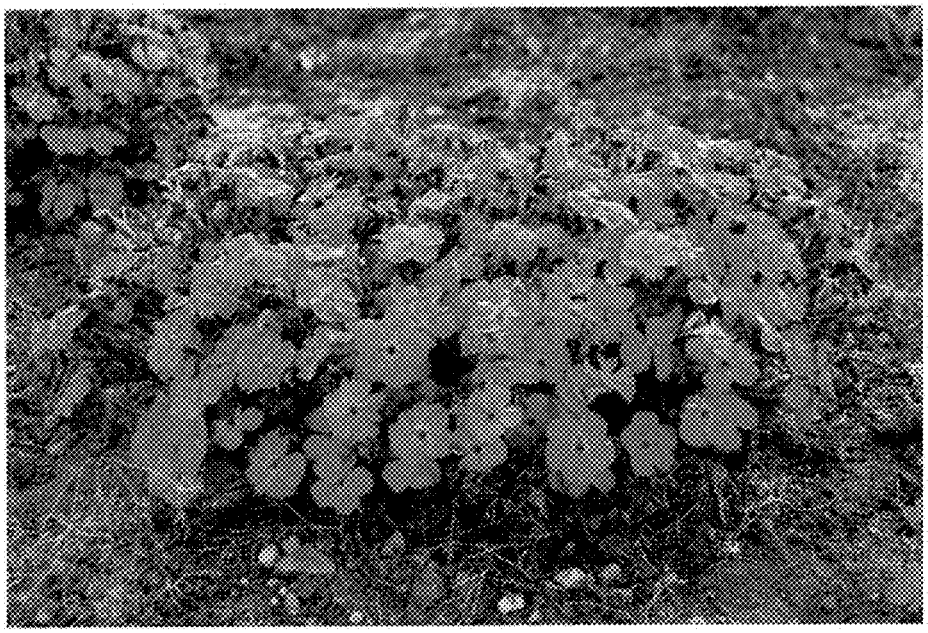
FIG. 1 shows the habit of the plant in mid-season flowering.
Figure 2:
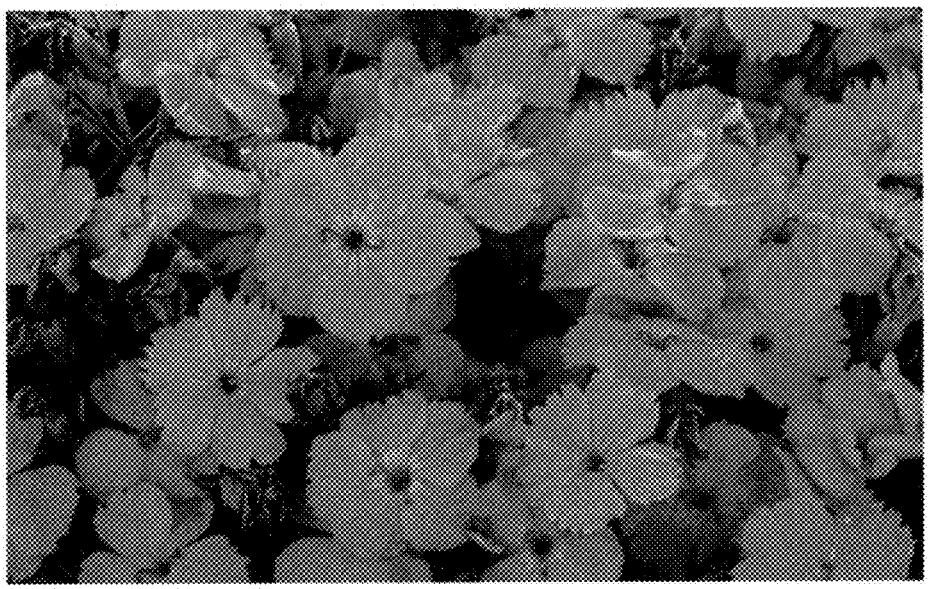
FIG. 2 shows a close-up of the flowers and buds.

The following detailed description of 'Pinky Promise' is based on observations of two-year-old plants in a full-sun trial garden at a nursery in Zeeland, Mich. with supplemental watering, light additions of fertilizer and free of other plant growth regulators. All color usage is in accordance with the 2015 edition of The Royal Horticultural Colour Chart except where common dictionary terms are used.

Botanical classification: *Dianthus* hybrid;

Parentage: The female or seed parent is 12-265-1; the male or pollen parent is 12-60-1;

Plant habit: Caespitose, herbaceous, evergreen, winter-hardy perennial; stems and peduncles highly branched, mostly erect stems to slightly arching; height of foliage about 14 cm and about 30 cm across; height in flower is about 16 cm;

*Root system*.—Fine, fibrous; color nearest RHS 155D depending on soil substrate and nutrition.

*Vigor*.—Very good, spring planted plugs finish in 3.8-liter pots in six to eight weeks.

Foliage:

*Leaf type*.—Simple; linear; opposite; decussate; sessile; glabrous; glaucous both adaxial and abaxial; margin entire; apex narrowly acute; base truncate, decurrent, clasping; reflex, arcuate downward; no fragrance detected; glaucosity light.

*Leaf dimensions*.—To about 35 mm long and about 7 mm wide near middle, average about 30 cm long and 5.5 mm wide.

*Leaf color*.—Young expanding adaxial base nearest RHS 145C and distally nearest RHS 137A, abaxial base nearest RHS 145C and distally nearest RHS 138B; mature adaxial base nearest RHS 145C and distally nearest RHS N138A, abaxial base nearest RHS 145C and distally nearest RHS N138A.

*Venation*.—Not pronounced; obscurely pinnate, coloration same as that of adaxial and abaxial.

Stems: About 100 per plant; upright and sprawling; cylindrical, not hollow; glabrous; glaucous; highly branching in upper nodes;

*Stem size*.—About 16 cm long to peduncle and about 1 mm wide at base.

*Stem color*.—Variable depending on light exposure, with little to no light exposure nearest RHS 145D, with moderate to high light exposure between RHS 138A and RHS 138B.

*Branching*.—Numerous; typically alternate from upper and lower nodes; about 12 per main stem and about 500 per plant in late spring peak; branch size average about 5.5 cm long and 1.0 mm diameter at time of initial flowering.

*Nodes*.—About 3 mm across; color nearest RHS 138B in high light and nearest RHS 145D in low light.

*Internodes*.—About 30 per stem before peduncle; average about 3 mm apart depending on growing temperature, shorter in cooler conditions.

*Inflorescence*.—Flowering in the upper 4 cm and to about 7 cm across; with an average of three flowers per inflorescence.

*Flower bud with calyx still closed*.—Slowly opening; glabrous; slightly glaucous; cylindrical with attenuate base and rounded apex; about 25 mm long and 5 mm across; without extrusion of styles.

*Flower bud color*.—With petals extended beyond calyx the distal petal portion nearest RHS NN74D, proximal petal portion nearest RHS 71C; calyx proximally between RHS 138A and RHS 138B, and proximally moderately tinted nearest RHS 187B.

Flower:

*Type*.—Terminal, cymose; perfect; salverform; actinomorphic; single.

*Attitude*.—Upright to slightly outwardly around perimeter of plant.

*Dimension*.—About 38 cm across and extending about 34 mm above base of calyx tube, calyx tube to about 26 mm tall and 5 mm wide at apex of calyx.

*Flowers per stem*.—Up to 3, average 2.5.

*Pedicel*.—Glaucous, glabrous, cylindrical, stiff; primarily upright.

*Pedicel size*.—Variable; to about 30 mm long and about 1.2 mm diameter; average about 10 mm long and 1.0 mm diameter.

*Pedicel color*.—Between N138A and RHS N189C.

*Flower period*.—Beginning in late May for about four weeks.

*Flower fragrance*.—Lightly sweet, spicy.

*Flower lasting quality*.—Individually about seven to ten days on or cut from plant.

*Corolla profile*.—Flat.

*Petals*.—Five; glabrous adaxial and abaxial except at proximal half of adaxial limb puberulent; consisting of a limb and a claw; limb obdeltoid, and limb and claw combined are flabellate; limb apex and margin finely to moderately dentate, with teeth about 1 mm to 2 mm long and 1 mm to 2 mm wide at base; limb base attenuate toward claw; claw with attenuate base; bent outwardly at limb base creating a flat rounded face; persistent; having a lighter eye.

*Petal dimensions*.—Limb to about 17 mm long and 17 mm wide; claw about 21 mm long and 6 mm wide tapering to attenuate base of about 1 mm across; whole petal to about 38 mm long, average about 36 mm long; lighter eye about 10 mm across, and darker bars about 0.5 mm wide and 1.5 mm long.

*Petal color*.—Young adaxial limb between RHS N74D and RHS NN74D, middle eye between RHS N74D and RHS 73B with bars of nearest RHS N74B, claw nearest RHS 145C proximally with distal claw portion before limb nearest RHS NN155C; young abaxial limb between RHS 73A and RHS N74D toward, claw nearest RHS 145C proximally with distal claw before limb nearest RHS NN155C; mature adaxial limb between RHS N74C and RHS N74B with center eye between RHS 75D and RHS 76D with darker veins of nearest RHS N74B extending about 6 mm from the eye into the limb, claw base nearest RHS 145D with middle nearest RHS 145C and distally nearest RHS NN155C; mature abaxial limb between RHS 73B and RHS N74D, claw base nearest RHS 145D, distal portion nearest RHS 145C.

*Calyx*.—Tubular; to about 26 mm long and 5 mm diameter at apex.

*Sepals*.—Five; acute apex and fused in basal 21 mm forming five-toothed calyx tube; glabrous adaxial and abaxial; glaucous abaxial; margins entire.

*Sepal size*.—Individually about 26 mm long and about 3 mm across at fusion.

*Sepal color*.—Adaxial nearest RHS 138A; abaxial proximally between RHS 138A and RHS 138B, and proximally moderately tinted nearest RHS 187B; with moderate anthocyanin observed.

*Peduncle*.—Glabrous; glaucous; hollow, cylindrical; stiff; about 3 cm long and about 2 mm diameter at base; attitude mostly upright to slightly arching.

*Peduncle color*.—Between RHS N138A and RHS 189B with light glaucous bloom.

*Epicalyx*.—Two pairs subtending each flower; both pairs adpressed; opposite; lightly glaucous, glabrous; sessile, margin entire; inner pair ovate to obtuse, narrowly acute apex and truncate base, 8 mm long and about 4 mm across near middle; outer pair lanceolate, with narrowly acute apex, truncate clasping base, about 12 mm long and about 4 mm wide;

*Epicalyx color*.—Both pairs adaxial and abaxial margin nearest RHS 145C and center to apex between RHS N138A and RHS 189B; faint anthocyanin pigment of nearest RHS 187B.

*Androecium*.—Typically 10; not fully developed; Filaments: straight; cylindrical; to about 15 mm long and 0.2 mm diameter; color nearest 15 RHS NN155B; Anther: oblong; basifixed; rudimentary; about 1 mm long and 0.3 mm across; color nearest RHS 76C; Pollen: abundant; color nearest RHS 160D.

*Gynoecium*.—Single; to about 28 mm long; Style: bifurcate just above ovary; shoulder absent; puberulent in adaxial distal one-third; curled with maturity; to 21 mm long and 1 mm across; color proximally nearest RHS NN155C, distal initially between RHS 72C and RHS 72B, distal with maturity nearest RHS N77A; Stigma: globose; puberulent along dorsal surface; about 0.5 mm long and 0.5 mm wide; color nearest RHS 72B; Ovary: superior; cylindrical; acute apex and truncate base; smooth, lustrous; about 7 mm long and 3 mm diameter; color distally nearest RHS 145A and proximally nearest RHS 150D.

Fruit: Not observed;

Disease resistance: The new plant is resistance to center die out from fungus or high temperatures.

Growth: The new plant grows best with adequate moisture and well-drained soil but is able to tolerate some drought once established. Hardiness at least from USDA zone 4 through zone 9.

It is claimed:

1. A new and distinct *Dianthus* plant named 'Pinky Promise' essentially as herein described and illustrated.

* * * * *